US009126974B2

(12) United States Patent
Yang et al.

(10) Patent No.: US 9,126,974 B2
(45) Date of Patent: *Sep. 8, 2015

(54) PROCESSES FOR THE PREPARATION OF PESTICIDAL COMPOUNDS

(71) Applicant: Dow AgroSciences LLC, Indianapolis, IN (US)

(72) Inventors: Qiang Yang, Zionsville, IN (US); Beth Lorsbach, Indianapolis, IN (US); Ronald Ross, Jr., Zionsville, IN (US); Kaitlyn Gray, Freeland, MI (US); Yu Zhang, Carmel, IN (US); Gary Roth, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/666,825

(22) Filed: Mar. 24, 2015

(65) Prior Publication Data

US 2015/0191448 A1 Jul. 9, 2015

Related U.S. Application Data

(63) Continuation of application No. 14/517,333, filed on Oct. 17, 2014.

(60) Provisional application No. 62/036,861, filed on Aug. 13, 2014, provisional application No. 62/001,929, filed on May 22, 2014, provisional application No. 61/892,137, filed on Oct. 17, 2013.

(51) Int. Cl.
| | | |
|---|---|---|
| C07D 401/04 | (2006.01) | |
| C07D 231/40 | (2006.01) | |
| A01N 43/56 | (2006.01) | |
| C07D 231/38 | (2006.01) | |

(52) U.S. Cl.
CPC .............. *C07D 401/04* (2013.01); *A01N 43/56* (2013.01); *C07D 231/38* (2013.01); *C07D 231/40* (2013.01)

(58) Field of Classification Search
None
See application file for complete search history.

(56) References Cited

U.S. PATENT DOCUMENTS

| | | |
|---|---|---|
| 3,597,341 A | 8/1971 | Oswald |
| 4,080,457 A | 3/1978 | Harrison et al. |
| 4,260,765 A | 4/1981 | Harrison et al. |
| 4,407,803 A | 10/1983 | Haviv et al. |
| 4,536,506 A | 8/1985 | Marcoux et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger |
| 7,192,906 B2 | 3/2007 | Hirohara et al. |
| 7,196,104 B2 | 3/2007 | Askew, Jr. et al. |
| 7,319,108 B2 | 1/2008 | Scwink et al. |
| 7,774,978 B2 | 8/2010 | Ding et al. |
| 7,803,832 B2 | 9/2010 | Critcher et al. |
| 7,910,606 B2 | 3/2011 | Nazare et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2 | 12/2014 | Buysse et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |

(Continued)

FOREIGN PATENT DOCUMENTS

| | | |
|---|---|---|
| EP | 0097323 | 1/1984 |
| EP | 0190457 | 8/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and—Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.

(Continued)

*Primary Examiner* — Timothy R Rozof
(74) *Attorney, Agent, or Firm* — Carl D. Corvin; Barnes & Thornburg LLP

(57) ABSTRACT

The present application provides processes for making pesticidal compounds and compounds useful both as pesticides and in the making of pesticidal compounds.

23 Claims, No Drawings

(56) References Cited

U.S. PATENT DOCUMENTS

| | | |
|---|---|---|
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2011/045224 | 10/2009 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2010/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/064324 | 5/2013 |
| WO | 2013/156431 | 10/2013 |
| WO | 2013/156433 | 10/2013 |

OTHER PUBLICATIONS

International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.

(56) References Cited

OTHER PUBLICATIONS

International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.

PROCESSES FOR THE PREPARATION OF PESTICIDAL COMPOUNDS

CROSS REFERENCE TO RELATED APPLICATIONS

This application is a continuation of U.S. application Ser. No. 14/517,333 filed on Oct. 17, 2014, which claims the benefit of U.S. Provisional Patent Applications: Ser. No. 62/036,861, filed Aug. 13, 2014; Ser. No. 62/001,929, filed May 22, 2014; and Ser. No. 61/892,137, filed Oct. 17, 2013, the entire disclosure of these applications are hereby expressly incorporated by reference in this Application.

TECHNICAL FIELD

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioethers and pesticidal sulfoxides efficiently and in high yield from commercially available starting materials.

DETAILED DESCRIPTION

The following definitions apply to the terms as used throughout this specification, unless otherwise limited in specific instances.

As used herein, the term "alkyl" denotes branched or unbranched hydrocarbon chains.

Unless otherwise indicated, the term "cycloalkyl" as employed herein alone is a saturated cyclic hydrocarbon group, such as cyclopropyl, cyclobutyl, cyclopentyl or cyclohexyl.

The term "thio" as used herein as part of another group refers to a sulfur atom serving as a linker between two groups.

The term "halogen" or "halo" as used herein alone or as part of another group refers to chlorine, bromine, fluorine, and iodine.

The compounds and process of the present application are described in detail below in Scheme 1.

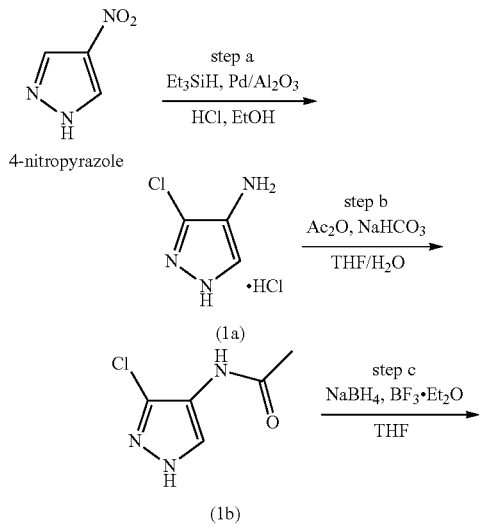

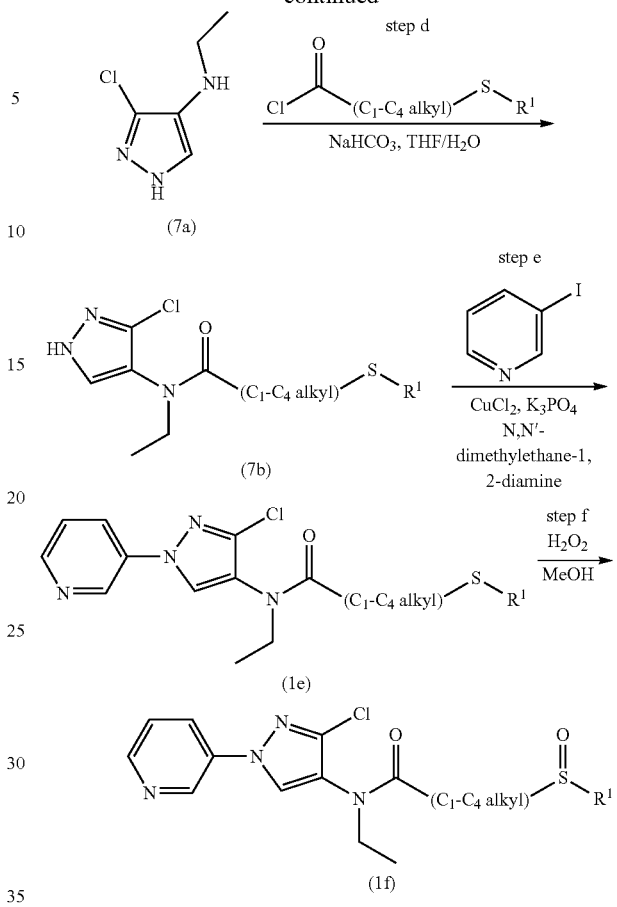

In step a of Scheme 1, 4-nitropyrazole is halogenated and reduced to yield 3-chloro-1H-pyrazol-4-amine hydrochloride (1a). The halogenation occurs at the 3-carbon through the use of concentrated (37 weight percent) hydrochloric acid (HCl). The reduction occurs with triethylsilane ($Et_3SiH$) and palladium on alumina ($Pd/Al_2O_3$) preferably about 1 to 10 weight percent palladium on alumina, more preferably about 5 weight percent. This reaction may be conducted at a temperature from about 0° C. to about 40° C., preferably about 10° C. to about 20° C. This reaction may be conducted in a polar protic solvent, such as methanol (MeOH) or ethanol (EtOH), preferably ethanol. It was surprisingly discovered, that by utilizing about 1 to about 4 equivalents, preferably, about 2.5 to about 3.5 equivalents of triethylsilane in this step, while conducting the reaction between about 10° C. and about 20° C., gives about a 10:1 molar ratio of the desired halogenated product 3-chloro-1H-pyrazol-4-amine hydrochloride (1a)

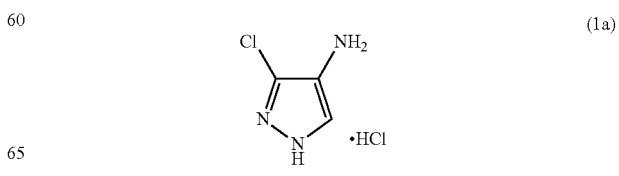

versus the undesired product

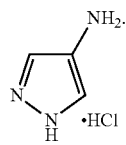

1H-pyrazol-4-amine hydrochloride

In step b of Scheme 1,3-chloro-1H-pyrazol-4-amine hydrochloride (1a) is acylated with acetic anhydride ($Ac_2O$) in the presence of a base, preferably an inorganic base, such as, sodium bicarbonate ($NaHCO_3$), at about 0° C. to about 40° C., preferably about 0° C. to about 20° C. to yield N-(3-chloro-1H-pyrazol-4-yl)acetamide (1b). It was surprisingly discovered that a chloro substituent must be present at the 3-position for this reaction to proceed to completion and to also avoid over acylation. Described herein is a comparative example without a halogen at the 3-position that yielded the double acylated product (see "CE-1"). Further, comparative example with a bromo group at the 3-position afforded the product in a surprisingly low yield compared to the yield with the chloro group (see "CE-2").

In step c of Scheme 1, N-(3-chloro-1H-pyrazol-4-yl)acetamide (1b) is reduced in the presence of a hydride source, preferably, sodium borohydride ($NaBH_4$), an acid source, such as a Brønsted acid or a Lewis acid, preferably a Lewis acid, preferably borontrifluoride etherate ($BF_3.Et_2O$) to yield 3-chloro-N-ethyl-1H-pyrazol-4-amine (7a). It has been surprisingly discovered that the yield of the reaction is greatly affected by the quality of the borontrifluoride etherate (purchased from different suppliers, currently, Sigma Aldrich product number 175501 being preferred).

In step d of Scheme 1,3-chloro-N-ethyl-1H-pyrazol-4-amine (7a) is reacted with an acyl chloride, indicated as $ClC(=O)C_1$-$C_4$-alkyl-S—$R^1$, to produce pesticidal thioether (1e). $R^1$ is selected from the group consisting of $C_1$-$C_4$-haloalkyl and $C_1$-$C_4$-alkyl-$C_3$-$C_6$-halocycloalkyl, preferably, $R^1$ is selected from $CH_2CH_2CF_3$ or $CH_2$(2,2-difluorocyclopropyl). The reaction is conducted in the presence of a base preferably, sodium bicarbonate to yield pesticidal thioether (7b). The coupling may be conducted in a mixture of tetrahydrofuran (THF) and water. It has been surprisingly discovered the thioether (7b) produced by this synthetic route is only monoacylated due to the presence of the chloro group at the 3-position of the pyrazole ring (See "CE-2"). It should be noted that that it was surprisingly found that the acyl chloride is important to use as opposed to activated carboxylic acids (see CE-4).

The acyl chloride, indicated as $ClC(=O)C_1$-$C_4$-alkyl-S—$R^1$, wherein $R^1$ is $CH_2CH_2CF_3$, can be prepared by the chlorination of 3-((3,3,3-trifluoropropyl)thio)propanoic acid with thionyl chloride. 3-((3,3,3-Trifluoropropyl)thio)propanoic acid may be prepared by the photochemical free-radical coupling of 3-mercaptopropionic acid with 3,3,3-trifluoropropene in the presence of 2,2-dimethoxy-2-phenylacetophenone initiator and long wavelength UV light in an inert organic solvent. While stoichiometric amounts of 3-mercaptopropionic acid and 3,3,3-trifluoropropene are required, because of its low boiling point, excess 3,3,3-trifluoropropene is usually employed to compensate for routine losses. From about 1 to about 10 mole percent initiator, 2,2-dimethoxy-2-phenylacetophenone, is typically used, with about 5 mole percent being preferred. Long wavelength UV light is sometimes called "black light" and ranges from about 400 to about 365 nanometers. The photochemical coupling is conducted in an inert organic solvent. Typical inert organic solvents must remain liquid to about −50° C., must remain relatively inert to the free radical conditions and must dissolve the reactants at reaction temperatures. Preferred inert organic solvents are aromatic and aliphatic hydrocarbons like toluene. The temperature at which the reaction is conducted is not critical but usually is from about −50° C. to about 35° C. Initially, it is important to keep the temperature below the boiling point of 3,3,3-trifluoropropene, i.e., about −18 to about −16° C. In a typical reaction, the inert organic solvent is cooled to less than about −50° C. and the 3,3,3-trifluoropropene is bubbled into the solvent. The 3-mercaptopropionic acid and 2,2-dimethoxy-2-phenylacetophenone are added and a long wave function (366 nm) UVP lamp (4 watt) is turned on. After sufficient conversion of 3-mercapto-propionic acid, the light is turned off and the solvent removed.

3-((3,3,3-Trifluoropropyl)thio)propanoic acid may also be prepared by the low temperature free-radical initiated coupling of 3-mercaptopropionic acid with 3,3,3-trifluoropropene in the presence of 2,2'-azobis(4-methoxy-2,4-dimethyl) valeronitrile (V-70) initiator at temperatures of about 0° C. to about 40° C. in an inert organic solvent. While stoichiometric amounts of 3-mercaptopropionic acid and 3,3,3-trifluoropropene are required, because of its low boiling point, excess 3,3,3-trifluoropropene is usually employed to compensate for routine losses. From about 1 to about 10 mole percent initiator, V-70, is typically used, with about 5 mole percent being preferred. The low temperature free-radical initiated coupling is conducted in an inert organic solvent. Typical inert organic solvents must remain liquid to about −50° C., must remain relatively inert to the free radical conditions and must dissolve the reactants at reaction temperatures. Preferred inert organic solvents are toluene (PhMe), ethyl acetate (EtOAc), and methanol. The temperature at which the reaction is conducted from about 0° C. to about 40° C. Initially, it is important to keep the temperature below the boiling point of 3,3,3-trifluoropropene, i.e., about −18 to about −16° C. The solution is cooled to less than about −50° C. and the 3,3,3-trifluoropropene is transferred into the reaction mixture. After stirring at room temperature for 24 hours, the reaction mixture is heated to about 50° C. for about 1 hour to decompose any remaining V-70 initiator followed by cooling and solvent removal.

In step e of Scheme 1, pesticidal thioether (7b) is reacting with a halopyridine, such as, 3-iodopyridine or 3-bromopyridine in the presence of a copper salt (such as copper(I) chloride (CuCl), copper(II) chloride ($CuCl_2$), and copper(I) iodide (CuI), preferably, CuCl), potassium carbonate ($K_2CO_3$), and N,N'-dimethylethane-1,2-diamine to yield pesticidal thioethers (1e). The process may be conducted in a polar solvent, such as, acetonitrile (MeCN), dioxane, or N,N-dimethylformamide at a temperature between about 50° C. and about 110° C. This synthetic method is simpler and reduces the costs of starting materials over known heteroarylation methods.

In step f of Scheme 1, thioether (1e) was oxidized with hydrogen peroxide ($H_2O_2$) in methanol to yield the desired pesticidal sulfoxides (1f).

EXAMPLES

The following examples are presented to better illustrate the processes of the present application.

Compound Examples

Example 1

3-chloro-1H-pyrazol-4-amine hydrochloride (1a)

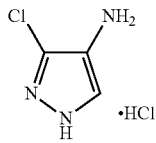

A 1000-mL, multi-neck cylindrical jacketed reactor, fitted with a mechanical stirrer, temperature probe and nitrogen (N₂) inlet, was charged with 4-nitropyrazole (50.0 g, 429 mmol) and palladium on alumina (5 weight %, 2.5 g). Ethanol (150 mL) was added, followed by a slow addition of concentrated hydrochloric acid (37%, 180 mL). The reaction was cooled to 15° C., and triethylsilane (171 mL, 1072 mmol) was added slowly via addition funnel over 1 hour, while maintaining the internal temperature at 15° C. The reaction was stirred at 15° C. for 72 hours, after which the reaction mixture was filtered through a Celite® pad and the pad was rinsed with warm ethanol (40° C., 2×100 mL). The combined filtrates were separated and the aqueous layer (bottom layer) was concentrated to ~100 mL. Acetonitrile (200 mL) was added and the resulting suspension was concentrated to ~100 mL. Acetonitrile (200 mL) was added and the resulting suspension was concentrated to ~100 mL. Acetonitrile (200 mL) was added and the resulting suspension was stirred at 20° C. for 1 hour and filtered. The filter cake was rinsed with acetonitrile (2×100 mL) and dried under vacuum at 20° C. to afford a white solid (~10:1 mixture of 1a and 1H-pyrazol-4-amine, 65.5 g, 99%): $^1$H NMR (400 MHz, DMSO-$d_6$) δ 10.52 (bs, 3H), 8.03 (s, 1H) EIMS: m/z 117.

Example 2

N-(3-chloro-1H-pyrazol-4-yl)acetamide (1b)

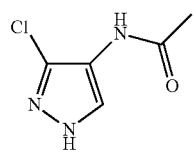

A 100-mL 3-neck round bottom flask was charged with 3-chloro-1H-pyrazol-4-amine hydrochloride (5.00 g, 32.5 mmol) and water (25 mL). Sodium bicarbonate (10.9 g, 130 mmol) was added slowly over 10 minutes (off-gassing during addition), followed by tetrahydrofuran (25 mL). The mixture was cooled to 5° C. and acetic anhydride (3.48 g, 34.1 mmol) was added over 30 minutes while maintaining the internal temperature at <10° C. The reaction was stirred at 5° C. for 1 hour, at which point thin layer chromatography (TLC) analysis [Eluent: ethyl acetate] indicated that the starting material had disappeared and a major product was exclusively formed. The reaction mixture was diluted with ethyl acetate (25 mL) and water (25 mL). The layers were separated and the aqueous layer was extracted with ethyl acetate (3×25 mL). The combined organic layers were concentrated to afford an off-white solid, which was suspended in methyl tert-butylether (20 mL), stirred for 1 hour, and filtered. The solid was rinsed with methyl tert-butylether (20 mL) and further dried under vacuum at room temperature (about 22° C.) for 4 hours to give a white solid (4.28 g, 83%): mp 162-164° C.; $^1$H NMR (400 MHz, DMSO-$d_6$) δ 12.90 (bs, 1H), 9.49 (s, 1H), 7.97 (s, 1H), 2.02 (s, 3H); $^{13}$C NMR (101 MHz, DMSO-$d_6$) δ 167.81, 130.07, 123.72, 116.73, 22.58; EIMS m/z 159 ([M]$^+$).

Example 3

3-Chloro-N-ethyl-1H-pyrazol-4-amine (7a)

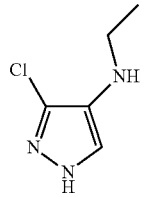

A 250-mL, 3-neck round bottom flask was charged with N-(3-chloro-1H-pyrazol-4-yl)acetamide (4.75 g, 29.8 mmol) and tetrahydrofuran (50 mL). Borontrifluoride etherate (7.8 mL, 74.4 mmol) was added and the mixture was stirred for 15 minutes. Sodium borohydride (3.38 g, 89 mmol) was added (off-gassing) and the reaction was heated at 50° C. for 4 hours, at which point thin layer chromatography analysis [Eluent: ethyl acetate, sample was prepared by treatment of reaction mixture with hydrochloric acid, followed by sodium bicarbonate basification and ethyl acetate extraction] indicated that the reaction was complete. Water (40 mL) was added (off-gassing), followed by concentrated hydrochloric acid (6 mL, off-gassing). The mixture was heated at 50° C. for 5 hours and allowed to cool to 20° C. and stirred for 16 hours. The mixture was concentrated under reduced pressure to remove tetrahydrofuran and basified with sodium bicarbonate. Ethyl acetate (50 mL) was added and the layers were separated. The aqueous layer was extracted with ethyl acetate (25 mL) and the combined organic layers were concentrated to dryness to afford a colorless oil (2.80 g, 65%): $^1$H NMR (400 MHz, DMSO-$d_6$) δ 12.30 (s, 1H), 7.20 (d, T=1.6 Hz, 1H), 3.94 (s, 1H), 2.87 (q, J=7.1 Hz, 2H), 1.11 (t, J=7.1 Hz, 3H); $^{13}$C NMR (101 MHz, DMSO) δ 129.18, 127.11, 115.03, 41.06, 14.56; EIMS m/z 145 ([M]$^+$).

Example 4

N-(3-chloro-1H-pyrazol-4-yl)-N-ethyl-3-((3,3,3-trifluoropropyl)thio)propanamide (Compound 4.7)

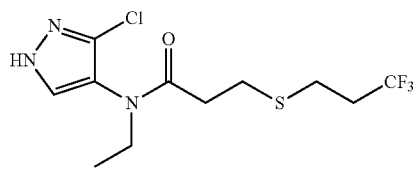 [SMILES: CCN(C(=O)CCSCCC(F)(F)F)c1c[nH]nc1Cl]

A 500-mL 3-neck flask was charged with 3-chloro-N-ethyl-1H-pyrazol-4-amine (3.25 g, 22.3 mmol), tetrahydrofuran (80 mL) and water (80 mL). The resulting suspension was cooled to 5° C. and sodium bicarbonate (3.75 g, 44.6 mmol) was added, followed by dropwise addition of 3-((3,3,3-trifluoropropyl)thio)propanoyl chloride (5.42 g, 24.56 mmol) at <5° C. The reaction mixture was stirred at <10° C. for 3 hours. The reaction mixture was poured into water (100 mL) and the mixture was extracted with dichloromethane (150 mL×3). The combined organics were washed with water (200 mL) and brine (200 mL), dried over anhydrous sodium sulfate (Na$_2$SO$_4$), filtered, and concentrated under reduced pressure to afford crude product as a light brown oil, which was purified by flash column chromatography using 0-5% methanol/dichloromethane as eluent. The fractions containing pure product were concentrated to give the desired product as a white solid (3.60 g, 48%): mp 67-68° C.; $^1$H NMR (400 MHz, CDCl$_3$) δ 11.55 (bs, 1H), 7.65 (s, 1H), 3.73-3.68 (dd, J$_1$=7.2, J$_2$=14.0, 2H), 2.86-2.82 (t, J=7.2, 2H), 2.67-2.63 (t, J=8.0, 2H), 2.45-2.30 (m, 4H), 1.16-1.12 (t, J=7.2, 3H); $^{13}$C NMR (101 MHz, CDCl$_3$) δ 171.87, 137.89, 128.40, 125.97 (q, J=277.4 Hz), 120.81, 44.01, 34.31 (q, J=27.3 Hz), 33.97, 27.30, 24.08 (q, J=3.4 Hz), 12.77; ESIMS m/z 330 ([M+H]$^+$).

Example 5

N-(3-chloro-1-(pyridin-3-yl)-1H-pyrazol-4-yl)-N-ethyl-3-((3,3,3-trifluoropropyl)thio)propanamide (Compound 5.7)

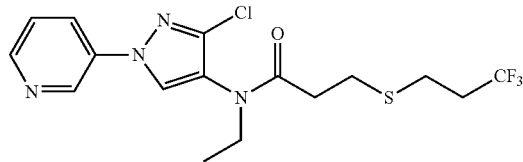 [SMILES: CCN(C(=O)CCSCCC(F)(F)F)c1cn(-c2cccnc2)nc1Cl]

To a dry 25-mL round bottom flask equipped with magnetic stirrer, and reflux condenser was charged 3-iodopyridine (78.0 mg, 0.378 mmol), and N-1H-pyrazol-4-yl)-N-ethyl-3-((3,3,3-trifluoropropyl)thio)propanamide (104 mg, 0.315 mmol) in 2.5 mL of anhydrous acetonitrile. N,N'-Dimethylethylene diamine (0.0180 mL, 0.158 mmol) and potassium carbonate (87.0 mg, 0.631 mmol) were added to form a colorless suspension. The reaction mixture was sparged with argon for 10 minutes, then added copper(I) chloride (6.2 mg, 0.063 mmol), and added another 2.5 mL of acetonitrile. The reaction was heated at 79° C. for 19 hours, at which point HPLC analysis indicated that the reaction was essentially complete. The reaction was poured into 25 mL of water, and the aqueous mixture was extracted with 3×10 mL of dichloromethane. The combined organic extracts were washed with water and brine, dried over anhydrous magnesium sulfate (MgSO$_4$), filtered, and concentrated. The resulting crude product was purified by flash column chromatography using 0-100% ethyl acetate/hexanes as eluent. The pure fractions were combined, and stripped to afford a yellow oil (85.0 mg, 66%): $^1$H NMR (400 MHz, DMSO-d$_6$) δ 9.09 (dd, J=2.6, 0.7 Hz, 1H), 8.96 (s, 1H), 8.60 (dd, J=4.8, 1.4 Hz, 1H), 8.23 (ddd, J=8.4, 2.7, 1.4 Hz, 1H), 7.60 (ddd, J=8.5, 4.8, 0.8 Hz, 1H), 3.59 (d, J=7.2 Hz, 2H), 2.74 (t, J=7.0 Hz, 2H), 2.65-2.56 (m, 2H), 2.57-2.44 (m, J=1.7 Hz, 2H), 2.40 (t, J=7.0 Hz, 2H), 1.08 (t, J=7.1 Hz, 3H); EIMS m/z 406 ([M]$^+$).

Example 6

N-(3-chloro-1-(pyridin-3-yl)-1H-pyrazol-4-yl)-N-ethyl-3-((3,3,3-trifluoropropyl)sulfoxo)propanamide (Compound 6.7)

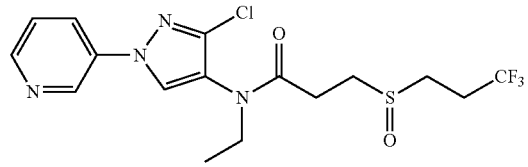 [SMILES: CCN(C(=O)CCS(=O)CCC(F)(F)F)c1cn(-c2cccnc2)nc1Cl]

N-(3-chloro-1-(pyridin-3-yl)-1H-pyrazol-4-yl)-N-ethyl-3-((3,3,3-trifluoropropyl)thio) propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate (Na$_2$CO$_3$). The organic layer was dried over sodium sulfate and concentrated to provide a thick yellow oil. The crude product was purified by flash column chromatography using 0-10% methanol/ethyl acetate as eluent and the pure fractions were combined and concentrated to afford the desired product as an oil (42.6 g, 68%): $^1$H NMR (400 MHz, DMSO-d$_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); IR (thin film) 1660 cm$^{-1}$; ESIMS m/z 423 ([M+H]$^+$).

Example 7

3-((3,3,3-trifluoropropyl)thio)propanoyl chloride

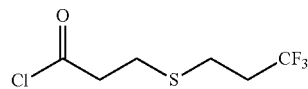

A dry 5 L round bottom flask equipped with magnetic stirrer, nitrogen inlet, reflux condenser, and thermometer, was charged with 3-((3,3,3-trifluoropropyl)thio)propanoic acid ((188 g, 883 mmol) in dichloromethane (3 L). Thionyl chloride (525 g, 321 mL, 4.42 mol) was then added dropwise over 50 minutes. The reaction mixture was heated to reflux (about 36° C.) for two hours, then cooled to room temperature. Concentration under vacuum on a rotary evaporator, followed by distillation (40 Torr, product collected from 123-127° C.) gave the title compound as a clear colorless liquid (177.3 g, 86%): $^1$H NMR (400 MHz, CDCl$_3$) δ 3.20 (t, J=7.1 Hz, 2H), 2.86 (t, J=7.1 Hz, 2H), 2.78-2.67 (m, 2H), 2.48-2.31 (m, 2H); $^{19}$F NMR (376 MHz, CDCl$_3$) δ −66.42, −66.43, −66.44, −66.44.

Example 8

3-((3,3,3-trifluoropropyl)thio)propanoic acid

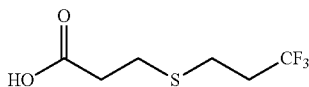

A 250 mL three-neck round bottom flask was charged with toluene (81 mL) and cooled to <−50° C. with a dry ice/acetone bath. 3,3,3-Trifluoropropene (10.28 g, 107.0 mmol) was bubbled into the solvent and the ice bath was removed. 3-Mercaptopropionic acid (9.200 g, 86.70 mmol) and 2,2-dimethoxy-2-phenylacetophenone (1.070 g, 4.170 mmol) was added and the long wave light (366 nm, 4 watt UVP lamp) was turned on (Starting temperature: −24° C.). The reaction reached a temperature of 27.5° C. due to heat from the lamp. The reaction was stirred with the black light on for 4 hours. After 4 hours the black light was turned off and the reaction concentrated by rotary evaporation (41° C., 6 mm Hg) giving a pale yellow oil (18.09 g, 51:1 linear:branched isomer, 90 wt % linear isomer by GC internal standard assay, 16.26 g active, 93%). The crude material was dissolved in 10% sodium hydroxide w/w (37.35 g) and was washed with toluene (30 mL) to remove non-polar impurities. The aqueous layer was acidified to pH ~2-3 with hydrochloric acid (2 N, 47.81 g) and was extracted with toluene (50 mL). The organic layer was washed with water (40 mL) and dried over magnesium sulfate, filtered, and concentrated by rotary evaporation giving a pale yellow oil (14.15 g, 34:1 linear:branched isomer, 94 wt % linear isomer by GC internal standard assay, 13.26 g active, 76%): $^1$H NMR (400 MHz, CDCl$_3$) δ 2.83 (td, J=7.1, 0.9 Hz, 2H), 2.76-2.64 (m, 4H), 2.47-2.30 (m, 2H); $^{13}$C NMR (101 MHz, CDCl$_3$) δ 177.68, 125.91 (q, J=277.1 Hz), 34.58 (q, J=28.8 Hz), 34.39, 26.63, 24.09 (q, J=3.3 Hz); $^{19}$F NMR (376 MHz, CDCl$_3$) δ −66.49.

Alternative synthesis of 3-((3,3,3-trifluoropropyl)thio)propanoic acid

A 100 mL stainless steel Parr reactor was charged with 3-mercaptopropionic acid (3.67 g, 34.6 mmol), toluene (30.26 g), and 2,2'-azobis(4-methoxy-2,4-dimethyl) valeronitrile (V-70, 0.543 g, 1.76 mmol) and the reactor was cooled with a dry ice/acetone bath, purged with nitrogen, and pressure checked. 3,3,3-Trifluoropropene (3.20 g, 33.3 mmol) was added via transfer cylinder and the reaction was allowed to warm to 20° C. After 24 hours, the reaction was heated to 50° C. for 1 hour to decompose any remaining V-70 initiator. The reaction was allowed to cool to room temperature. The solution was concentrated by rotary evaporation to provide the title compound (6.80 g, 77.5 wt % linear isomer by GC internal standard assay, 5.27 g active, 76%, 200:1 linear:branched by GC, 40:1 linear:branched by fluorine NMR)

Example 9

3-(((2,2-difluorocyclopropyl)methyl)thio)propanoic acid

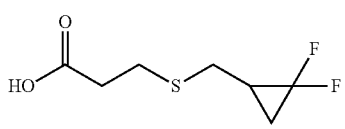 [SMILES: O=C(O)CCSCC1CC1(F)F]

Powdered potassium hydroxide (423 mg, 7.54 mmol) and 2-(bromomethyl)-1,1-difluorocyclopropane (657 mg, 3.84 mmol) were sequentially added to a stirred solution of 3-mercaptopropanoic acid (400 mg, 3.77 mmol) in methanol (2 mL) at room temperature. The resulting white suspension was stirred at 65° C. for 3 hours and quenched with 1N aqueous hydrochloric acid and diluted with ethyl acetate. The organic phase was separated and the aqueous phase extracted with ethyl acetate (2×50 mL). The combined organic extracts were dried over magnesium sulfate, filtered and concentrated in vacuo to give the title molecule as a colorless oil (652 mg, 84%): IR (thin film) 3025, 2927, 2665, 2569, 1696 cm$^{-1}$; $^1$H NMR (400 MHz, CDCl$_3$) δ 2.85 (t, J=7.0 Hz, 2H), 2.82-2.56 (m, 4H), 1.88-1.72 (m, 1H), 1.53 (dddd, J=12.3, 11.2, 7.8, 4.5 Hz, 1H), 1.09 (dtd, J=13.1, 7.6, 3.7 Hz, 1H); ESIMS m/z 195.1 ([M−H]$^-$).

Example 10

3-(((2,2-difluorocyclopropyl)methyl)thio)propanoyl chloride

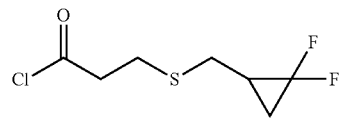 [SMILES: O=C(Cl)CCSCC1CC1(F)F]

In a 3 L 3 neck round bottomed-flask equipped with an overhead stirrer, a temperature probe, and addition funnel and an nitrogen inlet was charged with 3-(((2,2-difluorocyclopropyl)methyl)thio)propanoic acid (90.0 g, 459 mmol) that was immediately taken up in dichloromethane (140 mL) with stirring. At room temperature, thionyl chloride (170 mL, 2293 mmol) in dichloromethane (100 mL) was added drop-wise with stirring. The reaction mixture was heated to 40° C. and heated for 2 hours. The reaction was determined to be complete by $^1$H NMR (An aliquot of the reaction mixture was taken, and concentrated down via rotary evaporator). The reaction was allowed to cool to room temperature and the mixture was transferred to a dry 3 L round-bottom and concentrated via the rotary evaporator. This resulted in 95 g of a honey-colored oil. The contents were gravity filtered through paper and the paper rinsed with diethyl ether (10 mL). The rinse was added to the flask. This gave a clear yellow liquid. The liquid was placed on a rotary evaporator to remove the ether. This gave 92.4 g of a yellow oil. The oil was Kugelrohr distilled (bp 100-110° C./0.8-0.9 mm Hg) to provide the title compound as a colorless oil (81.4 g, 81%): $^1$H NMR (400 MHz, CDCl$_3$) δ 3.27-3.12 (m, 2H), 2.89 (t, J=7.1 Hz, 2H), 2.67 (ddd, J=6.8, 2.6, 1.0 Hz, 2H), 1.78 (ddq, J=13.0, 11.3, 7.4 Hz, 1H), 1.64-1.46 (m, 1H), 1.09 (dtd, J=13.2, 7.7, 3.7 Hz, 1H).

Biological Examples

Example A

Bioassays on Green Peach Aphid ("GPA") (*Myzus persicae*) (MYZUPE.)

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

Corrected % Control=100*(X−Y)/X where
X=No. of live aphids on solvent check plants and
Y=No. of live aphids on treated plants The results are indicated in the table entitled "Table 1: GPA (MYZUPE) and sweetpotato whitefly-crawler (BEMITA) Rating Table".

Example B

Bioassays on Sweetpotato Whitefly Crawler (*Bemisia tabaci*) (BEMITA.)

The sweetpotato whitefly, *Bemisia tabaci* (Gennadius), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective insecticides.

Cotton plants grown in 3-inch pots, with 1 small (3-5 cm) true leaf, were used at test substrate. The plants were placed in a room with whitely adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Pesticidal activity was measured by using Abbott's correction formula (see above) and presented in Table 1.

TABLE 1

| GPA (MYZUPE) and sweetpotato whitefly-crawler (BEMITA) Rating Table | | |
|---|---|---|
| Example Compound | BEMITA | MYZUPE |
| 1a | B | B |
| 1b | B | B |
| 7a | C | D |
| Compound 4.7 | C | D |
| Compound 5.7 | A | A |
| Compound 6.7 | A | A |

% Control of Mortality Rating
80-100 A
More than 0-Less than 80 B
Not Tested C
No activity noticed in this bioassay D

Comparative Examples

Example CE-1

N-(1-acetyl-1H-pyrazol-4-yl)acetamide

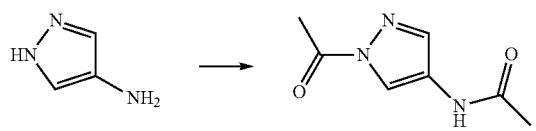

A 250-mL 3-neck flask was charged with 1H-pyrazol-4-amine (5 g, 60.2 mmol) and dichloromethane (50 mL). The resulting suspension was cooled to 5° C. and triethylamine (TEA, 9.13 g, 90.0 mmol) was added, followed by acetic anhydride (7.37 g, 72.2 mmol) at <20° C. The reaction was stirred at room temperature for 18 hours, at which point thin layer chromatography [Eluent: ethyl acetate] analysis indicated that the reaction was incomplete. Additional triethylamine (4.57 g, 45.0 mmol) and acetic anhydride (3.70 g, 36.0 mmol) were added and the reaction was heated at 30° C. for an additional 3 hours to give a dark solution, at which point thin layer chromatography analysis indicated that only a trace of starting material remained. The reaction mixture was purified by flash column chromatography using ethyl acetate as eluent. The fractions containing pure product were combined and concentrated to dryness to afford an off-white solid. The solid was dried under vacuum at room temperature for 18 hours (5.55 g, 55%): $^1$H NMR (400 MHz, DMSO-d$_6$) δ 10.30 (s, 1H), 8.39 (d, J=0.7 Hz, 1H), 7.83 (d, J=0.7 Hz, 1H), 2.60 (s, 3H), 2.03 (s, 3H); EIMS m/z 167 ([M]$^+$).

Example CE-2

N-(3-bromo-1H-pyrazol-4-yl)acetamide

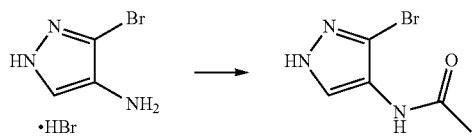

A 250 mL 3-neck round bottom flask was charged with 1H-pyraz-4-amine.hydrobromide (4.00 g, 24.7 mmol) and water (23 mL). To the mixture, sodium bicarbonate (8.30 g, 99.0 mmol) was added slowly over 10 minutes, followed by tetrahydrofuran (23 mL). The mixture was cooled to 5° C. and acetic anhydride (2.60 g, 25.4 mmol) was added over 30 minutes while maintaining the internal temperature at <10° C. The reaction mixture was stirred at −5° C. for 20 minutes, at which point $^1$H NMR and UPLC analyses indicated that the starting material was consumed and the desired product as well as bis-acetylated byproduct were formed. The reaction was extracted with ethyl acetate and the organic layers were dried over magnesium sulfate and concentrated. The crude mixture was triturated with methyl tert-butylether to remove the bisacetylated product to afford ~1.24 g of a white solid. $^1$H NMR analysis showed it was 1:1.1 desired to undesired bisacetylated product. The solid was purified by flash column chromatography using 50-100% ethyl acetate/hexanes as eluent to afford the desired product as a white solid (380 mg, 7.5%) and the bisacetylated product as a white solid (~800 mg): $^1$H NMR (400 MHz, DMSO-d$_6$) δ 13.01 (s, 1H), 9.36 (s, 1H), 7.92 (s, 1H), 2.03 (s, 3H); $^{13}$C NMR (101 MHz, DMSO) δ 167.94, 123.93, 119.19, 119.11, 22.63; ESIMS m/z 204 ([M+H]$^+$).

Example CE-4

1-(3-chloro-4-(ethylamino)-1H-pyrazol-1-yl)-3-((3,3,3-trifluoropropyl)thio)propan-1-one

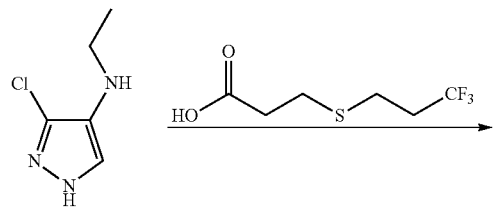

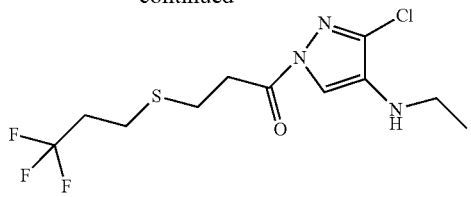

A 20-mL vial was charged with 3-chloro-N-ethyl-1H-pyrazol-4-amine (300 mg, 2.061 mmol) and acetonitrile (3 mL). Carbonyldiimidazole (CDI, 434 mg, 2.68 mmol) and 1H-imidazole hydrochloride (258 mg, 2.473 mmol) were added and the reaction was stirred at 20° C. for 4 hours. 3-Chloro-N-ethyl-1H-pyrazol-4-amine (300 mg, 2.061 mmol) was added and the reaction was stirred at 60° C. for 4 hours, at which point thin layer chromatography analysis [Eluent: 20% ethyl acetate/hexanes] indicated that the starting material disappeared and a major product formed. It was concentrated to dryness and the residue was purified by flash column chromatography using 20% ethyl acetate/hexanes as eluent. The pure fractions were concentrated to dryness to afford a colorless oil (520 mg, 77%): $^1$H NMR (400 MHz, CDCl$_3$) δ 7.49 (s, 1H), 3.32 (t, J=7.2 Hz, 2H), 3.18-2.98 (m, 3H), 2.95 (t, J=7.2 Hz, 2H), 2.84-2.64 (m, 2H), 2.53-2.27 (m, 2H), 1.27 (t, J=7.0 Hz, 3H); EIMS m/z 329 ([M]$^+$).

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A process for the preparation of thioether (7b) useful as a pesticide, (7b)

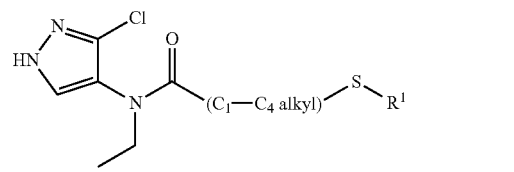

wherein R$^1$ is selected from the group consisting of C$_1$-C$_4$ haloalkyl and C$_1$-C$_4$ alkyl-C$_3$-C$_6$ halocycloalkyl, the process comprising acylating 3-chloro-N-ethyl-1H-pyrazol-4-amine (7a)

(7a)

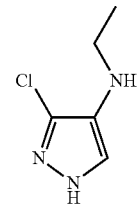

with an acyl chloride of the formula ClC(O)CH$_2$CH$_2$SR$^1$ in the presence of sodium bicarbonate in a mixture of tetrahydrofuran and water.

2. The process according to claim 1, wherein $R^1$ is $C_1$-$C_4$ haloalkyl.

3. The process according to claim 2, wherein R is $CH_2CH_2CF_3$.

4. The process according to claim 1, wherein $R^1$ is —$C_1$-$C_4$ alkyl-$C_3$-$C_6$ halocycloalkyl.

5. The process according to claim 4, wherein $R^1$ is

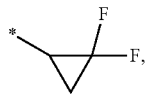

and * represents a covalent bond.

6. A process comprising:
(a) halogenating and reducing 4-nitropyrazole

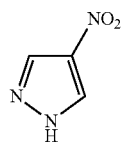

with concentrated hydrochloric acid at a temperature between about 0° C. and about 40° C. with between about 1 and about 4 equivalents of triethylsilane and about 5 weight percent palladium on alumina to yield 3-chloro-1H-pyrazol-4-amine hydrochloride (1a)

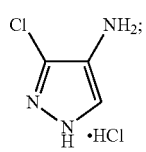

(b) mono-acylation of 3-chloro-1H-pyrazol-4-amine hydrochloride (1a) to yield

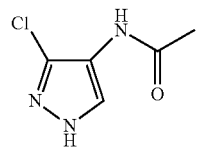

with acetic anhydride in the presence of a base at a temperature between about 0° C. and about 40° C.;
(c) reducing (1b) with a suitable reducing agent in the presence of a Lewis acid to yield 3-chloro-N-ethyl-1H-pyrazol-4-amine (7a)

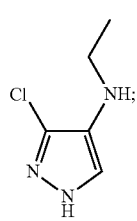

(d) contacting (7a) with an acid chloride of the formula Cl—C(O)—$C_1C_4$-alkyl-S—$R^1$, wherein $R^1$ is selected from the group consisting of $C_1$-$C_4$ haloalkyl and $C_1$-$C_4$ alkyl-$C_3$-$C_6$ halocycloalkyl, in the presence of a base to yield thioether (7b)

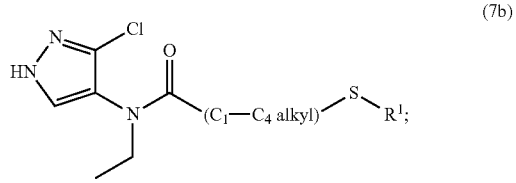

(e) contacting (7b) with a halopyridine in the presence of a copper salt, an amine and a base, at a temperature of between about 50° C. and about 110° C., to yield thioether (1e)

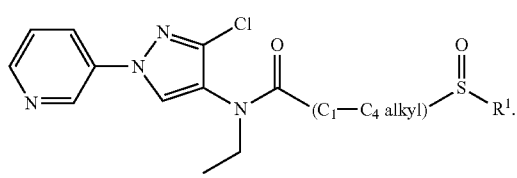

7. The process according to claim 6, wherein step (a) is carried at a temperature between about 10° C. and about 20° C.

8. The process according to claim 6, wherein step (a) is carried out in a polar protic solvent.

9. The process according to claim 8, wherein step (a) is carried out in a polar protic solvent is methanol or ethanol.

10. The process according to claim 7, wherein step (a) is carried out with between about 2.5 and about 3.5 equivalents of triethylsilane.

11. The process according to claim 6, wherein the base in step (b) is sodium bicarbonate.

12. The process according to claim 6, wherein the temperature of step (b) is between about 0° C. and about 40° C.

13. The process according to claim 12, wherein the reducing agent in step (c) is sodium borohydride.

14. The process according to claim 12, wherein the Lewis acid in step (c) is borontrifluoride etherate.

15. The process according to claim 6, wherein the base in step (d) is sodium bicarbonate.

16. The process according to claim 15, wherein $R^1$ is $CH_2CH_2CF_3$.

17. The process according to claim 15, wherein $R^1$ is

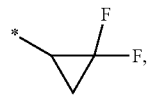 [SMILES: *C1CC1(F)F]

and * represents a covalent bond.

18. The process according to claim 6, wherein the halopyridine in step (e) is 3-bromopyridine.

19. The process according to claim 18, wherein the copper salt of step (e) is copper (I) chloride, copper (II) chloride or copper (I) iodide.

20. The process according to claim 19, wherein the amine of step (e) is N,N'-dimethylethane-1,2-diamine.

21. The process according to claim 20, wherein the base of step (e) is potassium carbonate.

22. The process according to claim 6, further comprising the step of contacting the thioether of the formula (1e)

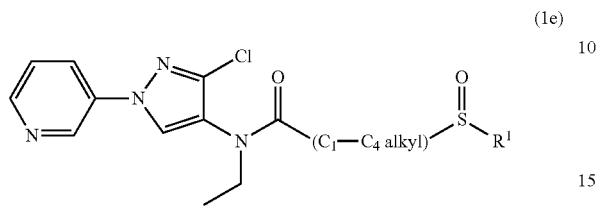

with an oxidizing agent to provide a pesticidal sulfoxide of the formula (1f)

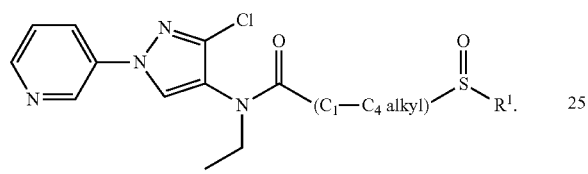

23. The process of claim 22, wherein the oxidizing agent is hydrogen peroxide in methanol.

* * * * *

UNITED STATES PATENT AND TRADEMARK OFFICE
CERTIFICATE OF CORRECTION

| | |
|---|---|
| PATENT NO. | : 9,126,974 B2 |
| APPLICATION NO. | : 14/666825 |
| DATED | : September 8, 2015 |
| INVENTOR(S) | : Qiang Yang et al. |

Page 1 of 1

It is certified that error appears in the above-identified patent and that said Letters Patent is hereby corrected as shown below:

Claims

Column 16, lines 25-30 claim 6, should read

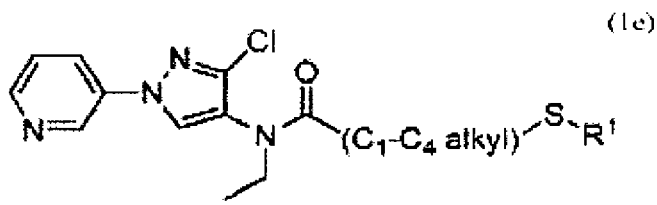

Column 17, lines 10-15 claim 22, should read

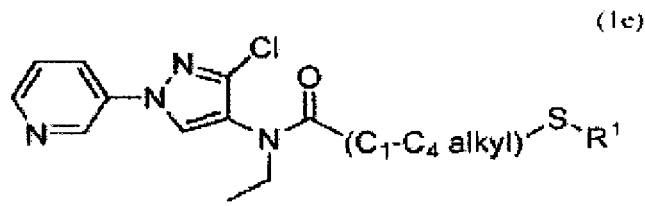

Signed and Sealed this
Twenty-second Day of March, 2016

Michelle K. Lee
*Director of the United States Patent and Trademark Office*